(12) United States Patent
Hong

(10) Patent No.: US 10,857,091 B2
(45) Date of Patent: Dec. 8, 2020

(54) FERMENTED COMPOSITION FOR PREVENTING HAIR LOSS AND PROMOTING HAIR GROWTH CONTAINING NATURAL EXTRACTS

(71) Applicant: Truezyme Co., Ltd., Ulsan (KR)

(72) Inventor: Kyu Ree Hong, Ulsan (KR)

(73) Assignee: Truezyme Co., Ltd., Ulsan (KR)

( * ) Notice: Subject to any disclaimer, the term of this patent is extended or adjusted under 35 U.S.C. 154(b) by 215 days.

(21) Appl. No.: 15/820,329

(22) Filed: Nov. 21, 2017

(65) Prior Publication Data

US 2018/0140541 A1 May 24, 2018

(30) Foreign Application Priority Data

Nov. 22, 2016 (KR) ........................ 10-2016-0155832

(51) Int. Cl.
| | |
|---|---|
| *A61Q 7/00* | (2006.01) |
| *A61Q 5/02* | (2006.01) |
| *A61K 8/34* | (2006.01) |
| *A61K 47/46* | (2006.01) |
| *A61K 35/747* | (2015.01) |
| *A61K 36/752* | (2006.01) |
| *A61K 36/725* | (2006.01) |
| *A61K 36/48* | (2006.01) |
| *A61K 8/99* | (2017.01) |
| *A61K 8/9789* | (2017.01) |

(52) U.S. Cl.
CPC ................. *A61K 8/99* (2013.01); *A61K 8/34* (2013.01); *A61K 8/9789* (2017.08); *A61Q 7/00* (2013.01); *A61K 2800/5922* (2013.01); *A61K 2800/85* (2013.01); *A61Q 5/02* (2013.01)

(58) Field of Classification Search
None
See application file for complete search history.

(56) References Cited

U.S. PATENT DOCUMENTS

| | | | | |
|---|---|---|---|---|
| 2006/0018867 | A1* | 1/2006 | Kawasaki | A61K 8/898 424/70.122 |
| 2008/0292751 | A1* | 11/2008 | Ogasawara | C12N 1/20 426/43 |

OTHER PUBLICATIONS

Higashi-Okai. Phytother. Res. 16, 781-784. (Year: 2002).*
Jin-wei. Process Biochemistry 40 (2005) 3607-3613 (Year: 2005).*
Chen.Journal of Chromatography A, 1227 (2012) 145-153. (Year: 2012).*
Lin. J. Agric. Food Chem. 2005, 53, 3795-3800 (Year: 2005).*

* cited by examiner

*Primary Examiner* — Nicole P Babson
*Assistant Examiner* — Lori K Mattison
(74) *Attorney, Agent, or Firm* — Sughrue Mion, PLLC

(57) ABSTRACT

Provided is a composition for preventing hair loss and promoting hair growth, including a mixed extract consisting of a *Lactobacillus*-fermented product, a citrus (Citrus unshiu Marcov.) peel extract, a Glycine max embryo extract, a Nelumbo nucifera extract, and a Ziziphus jujube Mill extract as an active ingredient.

10 Claims, No Drawings

FERMENTED COMPOSITION FOR PREVENTING HAIR LOSS AND PROMOTING HAIR GROWTH CONTAINING NATURAL EXTRACTS

CROSS-REFERENCE TO RELATED APPLICATION

This application claims priority to and the benefit of Korean Patent Application No. 2016-0155832, filed on Nov. 22, 2016, the disclosure of which is incorporated herein by reference in its entirety.

BACKGROUND

1. Field of the Invention

The present invention relates to a composition capable of promoting hair growth while minimizing hair damage and irritation.

2. Discussion of Related Art

In animals, hair is entirely replaced during molting season, but in humans, some of the total hair is replaced every day, and the number of hairs remains constant.

The hair cycle is divided into three phases of anagen, catagen, and telogen. In anagen, cell division is active in the papillae, and hair growth is promoted.

The hair growth cycle is about 3 to 5 years for males and about 4 to 6 years for females, and about 80 to 85% of hair is present during anagen phase. In catagen, cell division is gradually stopped, and the duration of catagen is about 3 to 4 weeks. In telogen, the papillae are contracted, and hair is separated from the capillaries. As a result, hair is simply embedded in the scalp. The duration of telogen is about 3 months. The hair present in telogen is easily removed from the scalp by physical stimulation.

Human hair, though unrelated to life, may have a decisive impact on human impressions and appearance. Therefore, interest in hair is growing socially. Furthermore, in the past, hair loss was recognized as a simple symptom, but recently it has been recognized as a disease.

Recently, the number of people suffering from hair loss has been rapidly increasing due to excessive stress caused by industrialization and socio-cultural factors such as lifestyle. In addition, hair loss is increasing in elderly persons as well as middle-aged men. Accordingly, research for finding various causes of hair loss and treating hair loss has been actively conducted.

In addition, in the cosmetics industry, a number of products containing natural products are being developed to reduce skin irritation caused by various chemical substances. Due to the small side effects of natural ingredients on the skin, demand for cosmetics using natural ingredients is increasing. Therefore, the value of natural products as cosmetics ingredients is increasing.

Therefore, research on development of multifunctional cosmetics having excellent biosafety and skin improvement effect is being actively carried out.

SUMMARY OF THE INVENTION

Therefore, the present invention has been made in view of the above problems, and it is an objective of the present invention to provide a composition for preventing hair loss and promoting hair growth including natural raw materials as active ingredients. The composition of the present invention is beneficial to skin health and has an excellent effect in preventing hair loss and promoting hair growth.

In accordance with the present invention, the above and other objectives can be accomplished by the provision of a composition for preventing hair loss and promoting hair growth including a mixed extract consisting of a *Lactobacillus*-fermented product, a citrus (Citrus unshiu Marcov.) peel extract, a Glycine max embryo extract, a Nelumbo nucifera extract, and a Ziziphus jujube Mill extract, as an active ingredient.

In one embodiment, the mixed extract may contain 10 to 20 parts by weight of the *Lactobacillus*-fermented product, 10 to 20 parts by weight of the citrus (Citrus unshiu Marcov.) peel extract, 10 to 20 parts by weight of the Glycine max embryo extract, 10 to 20 parts by weight of the Nelumbo nucifera extract, and 10 to 20 parts by weight of the Ziziphus jujube Mill extract.

In one embodiment, the composition may contain 0.5 to 10.0% by weight of the mixed extract.

In one embodiment, the mixed extract may be extracted using one or more solvents selected from the group consisting of purified water, a lower alcohol having 1 to 4 carbon atoms, acetone, ethyl acetate, butyl acetate, and 1,3-butylene glycol.

In one embodiment, the alcohol may be 60 to 90% (v/v) ethanol.

In one embodiment, the composition may have anti-inflammatory and antimicrobial activities and ability to promote cell proliferation.

In one embodiment, the composition may be formulated into one or more selected from the group consisting of hair toner, hair lotion, hair cream, hairspray, hair mousse, hair gel, hair soap, hair shampoo, hair conditioner, hair pack, and hair treatment.

In one embodiment, the composition may be formulated into liquid hair shampoo.

DETAILED DESCRIPTION OF EXEMPLARY EMBODIMENTS

Although the terms used in the present invention are selected from generally known and used terms, terms used herein may be variable depending on operator's intention or customs in the art, appearance of a new technology, or the like. In addition, some of the terms mentioned in the description of the present invention have been selected by the applicant at his or her discretion, the detailed meanings of which are described in relevant parts of the description herein. Furthermore, it is required that the present invention is understood, not simply by the actual terms used but by the meanings of each term lying within.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The numerical range includes numerical values defined in the above range. All maximum numerical limitations given throughout this specification include all lower numerical limitations, as lower numerical limitations are explicitly stated. All minimum numerical limitations given throughout this specification include all higher numerical limitations as higher numerical limitations are explicitly stated. All numerical limitations given throughout this specification will include any better numerical range within broader numerical range, as narrower numerical limitations are explicitly stated.

Hereinafter, embodiments of the present invention will be described in detail, but it should be apparent that the present invention is not limited by the following embodiments.

According to an aspect of the present invention, provided is a composition for preventing hair loss and promoting hair growth including a mixed extract consisting of a *Lactobacillus*-fermented product, a citrus (Citrus unshiu Marcov.) peel extract, a *Glycine max* embryo extract, a *Nelumbo nucifera* extract, and a *Ziziphus jujube* Mill extract as an active ingredient.

The composition for preventing hair loss and promoting hair growth includes a mixed extract derived from natural raw materials as an active ingredient. Thus, the composition has an excellent effect in preventing hair loss and promoting hair growth. In addition, the composition is safe for the human body and may minimize skin irritation when applied to skin. Since the mixed extract acts on the human body in a complex manner, the effect of preventing hair loss and promoting hair growth may be remarkably enhanced as compared to a single extract.

In addition to the hair growth promoting effect, the composition may have anti-inflammatory and antimicrobial activities and ability to promote cell proliferation. Thus, the composition may have excellent effects on preventing dandruff and relieving scalp inflammation.

The *Lactobacillus*-fermented fermented product refers to a mixture of fermented products obtained by fermenting a medium containing energy sources such as skim milk powder using a *Lactobacillus* strain. The fermented products may be prepared by a conventional fermentation method using lactic acid bacteria. The fermentation method using lactic acid bacteria is well known to those skilled in the art.

The energy source may be cow milk, goat milk or horse milk, and these milks may be used in the form of whole milk, skim milk or powdered milk.

The *Lactobacillus* strain may be *Lactobacillus pentosus, Lactobacillus brevis, Lactobacillus plantarum, Lactobacillus casei* or *Lactobacillus acidophilus*, without being limited thereto.

The term "citrus (Citrus unshiu Marcov.)" is rich in vitamin C and citric acid, and contains vitamin P, phosphorus, and hesperidin, which are excellent in strengthening capillary blood vessels. The active ingredients are more abundant in the peel than in the flesh, and for example, vitamin C is about four times more abundant in the peel than in the flesh. The citrus (Citrus unshiu Marcov.) peel extract has an excellent effect of neutralizing IL-8, an inflammatory cytokine, and neutralizes melanocyte-stimulating substances, thereby inhibiting melanin production. Thus, the citrus (Citrus unshiu Marcov.) peel extract may help to make the scalp healthy and clean.

The term "Glycine max" may be SEORITAE, SEOMOKTAE, HEUKTAE, HWANGTAE, green bean (CHEONGTAE), kidney bean, speck kidney bean, hedge bean, mung bean, red bean, big bean, soybean sprout, SEONBI bean or soybean, without being limited thereto. The Glycine max embryo contains isoflavone and phospholipids, which are useful physiologically active substances in the human body, and also contains a large amount of embryo-specific components such as glycitein, soy saponins A1 and A4, and phytic acid.

The term "Nelumbo nucifera" refers to a perennial plant that lives in ponds and reservoirs, and major components contained in the calyx thereof include d-(−)-N-norarmepavine, liriodenine, N-nornuciferine, and nuciferine. A large amount of flavonoids, such as luteolin-7-glucoside, quercetin-7-glucoside, and kaempferol-3-glucosylglucoside, is included in the petal. Nelumbo nucifera is used for stypsis, hemostasis, ganacratia, HYEOLBUNG (vulvar bleeding), anal fistula, hematemesis, neurasthenia, and the like.

The term "Ziziphus jujube Mill" refers to a thorny rhamnaceous plant belonging to the Buckthorn family (Rhamnaceae), and fruits thereof are mainly used. Ziziphus jujube Mill is rich in nutritional ingredients and is widely used in oriental medicine. Ziziphus jujube Mill basically contains a lot of saccharides and ascorbic acid. In addition, medicinal components including various sterols, alkaloids, saponins, vitamins, organic acids, amino acids, and the like are contained. Ziziphus jujube Mill has been widely used in the pharmaceutical industry since pharmacological effects thereof have been confirmed, and is used for alleviators, diuretics, dynamophores, hemobilia, hyperthelesia, recovery of physical strength, apophlegmatic agents, and anti-inflammatory agents.

The mixed extract may contain 10 to 20 parts by weight of the *Lactobacillus*-fermented product, 10 to 20 parts by weight of the citrus (Citrus unshiu Marcov.) peel extract, 10 to 20 parts by weight of the Glycine max embryo extract, 10 to 20 parts by weight of the Nelumbo nucifera extract, and 10 to 20 parts by weight of the Ziziphus jujube Mill extract.

The term "extract" refers to a solvent containing the active ingredients of a raw material, and may be obtained by mixing a solvent and the raw material under specific conditions.

The mixed extract may be extracted using one or more solvents selected from the group consisting of purified water, a lower alcohol having 1 to 4 carbon atoms, acetone, ethyl acetate, butyl acetate, and 1,3-butylene glycol, and the alcohol may be 60 to 90 ethanol.

The extraction proportion of active ingredients contained in the raw material may be varied depending on the polarity of a solvent. Since ethanol may selectively extract physiologically active substances from a natural raw material, the effect of promoting hair growth may be realized when an extract obtained by ethanol extraction is used.

Particularly, water and ethanol have different polarities, and thus active ingredients to be extracted may vary depending on the net polarity of the mixture of water and ethanol. Therefore, the concentration of ethanol may be appropriately controlled to enhance the effect of promoting hair growth. At this time, when the concentration of ethanol exceeds 90%, the yield of an extract may be low. When the concentration of ethanol is less than 60%, active ingredients responsible for promoting hair growth may not be extracted sufficiently.

The method of preparing the mixed extract is as follows. First, each raw material is washed with water, dried, and then pulverized. After adding a solvent having a volume corresponding to 8 to 12 times the weight of the pulverized product to the pulverized product, an extraction process is performed for about 1 to 24 hours according to a conventional extraction method. At this time, examples of the extraction method include reflux circulation extraction, pressure extraction, ultrasonic extraction, and the like. Finally, a filtration process is performed. In addition, the extract may be obtained in a powder form by an additional process such as vacuum distillation or lyophilization.

Examples of the extract may include extracts that have been subjected to a conventional purification process. Specific examples of the extract may include extracts obtained by additionally performing various purification processes such as separation using an ultrafiltration membrane having a constant molecular weight cut-off value and separation using chromatography (separation by size, charge, hydrophobicity or affinity).

In addition, the mixed extract may be extracted using alkaline ionized water. The alkaline ionized water refers to water containing alkaline minerals. Typically, alkaline ionized water may be prepared by electrolyzing drinking water, and the concentration of hydrogen ion (pH) may be about 8.0 to 12.0. Alkaline ionized water is rapidly absorbed in the human body and may be discharged to the outside of the human body in combination with acidic waste matters. In addition, alkaline ionized water is effective for prevention and treatment of adult diseases. When pregnant women drink alkaline ionized water, alkaline ionized water may promote development of the brain and bones of a fetus and may alleviate morning sickness.

When alkaline ionized water is used as a solvent, since alkaline ionized water contains general water-soluble components and has lipolytic properties, fat-soluble active ingredients are also extracted. Therefore, alkaline ionized water has improved extraction ability. In particular, since unnecessary components extracted at low pH are not extracted, effects of preventing hair loss and promoting hair growth of the composition may be remarkably improved.

Alkaline ionized water may be generated in a cathode region when cathode (−) and anode (+) electrodes are placed in a water tank, and electrolysis is performed. The generated alkaline ionized water may be used as a solvent.

The composition may contain 0.5 to 10.0% by weight of the mixed extract. When the mixed extract is contained in an amount less of than 0.5% by weight, the effect of promoting hair growth by the mixed extract may not be properly realized. When the mixed extract is contained in an amount exceeding 10.0% by weight, the amount of other additives to be contained in a product is reduced, and thus the quality of the product may deteriorate.

The composition for preventing hair loss and promoting hair growth may further include amino acid complexes, hydrolyzed silk, fragrance ingredients, ceramide, and excipients.

The amino acid complex refers to a complex composition including at least one amino acid, which is a basic constituent unit of a protein, and the type of the amino acid or the mixing ratio of the amino acids is not particularly limited and may be varied as needed. The amino acid complex has a skin moisturizing effect and imparts shine to the hair, thereby enhancing the efficacy of the composition and minimizing irritation to the skin.

The hydrolyzed silk refers to water or diluted ethanol containing peptides obtained by hydrolyzing fibroin with an acid or alkali solvent, and may often be used for a skin or hair conditioning agent. Since the hydrolyzed silk contains the constituents of a protein, it is safe for the human body. In addition, the hydrolyzed silk may impart shine and elasticity to the hair and restore damaged hair.

The fragrance ingredient refers to a substance to be added to food, cosmetics or the like to produce a fragrance. The fragrance ingredient is easily volatilized at room temperature and may be added as needed for the commercialization of the composition. The kind of the fragrance ingredient is not particularly limited, and aromatic chemicals, essential oil, natural extracts, distillate, isolated ingredients, aroma, resins, and the like may be used as the fragrance ingredient.

The ceramide is a type of lipid, accounting for about 40% or more of the lipids of keratinocytes constituting the stratum corneum, and is an essential component in the structure and function of the stratum corneum. Since ceramide has both hydrophilic and lipophilic groups, when a composition containing ceramides is applied to the skin, evaporation of water in the skin may be suppressed. Ceramide may be used as a raw material for a moisturizing agent because ceramide forms a water film on the hair to inhibit water evaporation and prevent skin damage.

The excipient refers to a substance that is added to impart a suitable hardness or shape to a medicament or to a substance that is added to make a major medicament easier to handle when the size of the major medicament is insufficient. The kind of the excipient is not particularly limited, and lactose, starch, dextrin, glycerin, cellulose, and the like may be included.

In addition to the additives, the composition may contain various additives such as emulsifiers, preservatives, diluents, and pigments in consideration of the functions and uses of the composition.

The composition may further include a base component which may be combined with a common external preparation for the scalp and the hair. Specific examples of the base component may include solubilizing agents, surfactants, moisturizers, thickeners, pH adjusters, antiseptics, antioxidants, sequestrants, germicides, anti-inflammatory agents, antimicrobial agents, solvents, coloring agents, fragrance ingredients or the like.

The solubilizing agents may include isopropyl myristates, polyethylene glycols, medium-chain triglycerides, hydrocarbons, glycols, and the like.

Among the surfactants, anionic surfactants may include ammonium lauryl sulfosuccinate, ammonium lauryl sulfate, sodium cocoyl isethionate, sodium lauryl isethionate, sodium lauryl sulfate, triethanolamine lauryl sulfate, sodium lauryl ether sulfate (1 to 3 ethylene oxides), and the like. Nonionic surfactants may include polyoxyethylene alkyl ethers, polyoxyethylene fatty acid esters, polyoxyethylene, hardened castor oil derivatives, fatty acid diethanolamides, glyceryl stearate, and the like. Cationic surfactants may include tertiary aliphatic amine salts, alkyltrimethylammonium chloride, dialkyldimethylammonium chloride, and the like. Amphoteric surfactants may include betaine, betaine amide, sulfobetaine, steartrimonium chloride, and the like.

The moisturizers may include glycerin, propylene glycol, 1,3-butylene glycol, dipropylene glycol, sorbitol, and the like.

The thickeners may include water-soluble polymeric compounds such as methylcellulose, hydroxyethyl cellulose, carrageenan, carboxymethyl cellulose, and hydroxymethyl cellulose.

Specific examples of the pH adjusters may include citric acid, sodium hydroxide, triethanolamine, sodium citrate, phosphoric acid, sodium phosphates, lactic acid, and the like.

The antiseptics may include benzoic acid, ρ-hydroxybenzoate esters, the mixtures of methylchloroisothiazolinone, phenoxyethanol, DMDM hydantoin, and the like. The antioxidants may include dibutyl hydroxy toluene (BHT), ascorbic acid, and the like.

The sequestrants may include disodium ethylenediaminetetraacetate, tetrasodium ethylenediaminetetraacetate, and the like. The germicides may include chlorhexidine gluconate, quaternary ammonium salts, piroctone olamine, zinc pyrithione suspension, iodopropynyl butylcarvamate, salicylic acid, and the like.

The anti-inflammatory agents may include monoammonium glycyrrhizinate, dipotassium glycyrrhizinate, stearyl glycyrrhizinate, camomile, alpha-bisabolol, allantoin, and the like. Specific examples of the antimicrobial agents may include phenoxyethanol, chlorhexidine, chlorhexidine gluconate, piroctone olamine, ketoconazole, arnica extracts, iodopropynyl butylcarbamate, benzalkonium chloride, benzethonium chloride, benzoic acid and salts thereof, benzyl alcohol, lavender, rosemary, salicylic acid, triclocarbon, zinc pyrithione suspension, and the like.

The solvents may include ethanol, purified water, Tween 20, cyclomethicone, mineral oil, dimethicone, and the like. The coloring agents and fragrance ingredients may include conventional agents used in scalp and hair formulations.

In addition, the composition may be formulated into a hair treatment composition such as emulsion, cream, paste, gel, face lotion, pack, lotion, powder, spray, and soap. Specifically, the composition may be formulated into one or more selected from the group consisting of hair toner, hair lotion, hair cream, hairspray, hair mousse, hair gel, hair soap, hair shampoo, hair conditioner, hair pack, and hair treatment (e.g., liquid hair shampoo).

In the formulations, ingredients other than the above-mentioned essential ingredients may be appropriately selected and blended by those skilled in the art depending on the use or purpose of an external preparation containing the composition of the present invention.

For example, when the formulation of the composition is paste, cream or gel, animal fibers, plant fibers, wax, paraffin, starch, tragacanth, cellulose derivatives, polyethylene glycol, silicone, bentonite, silica, talc or zinc oxide may be used as a carrier ingredient.

When the formulation of the composition is powder or spray, lactose, talc, silica, aluminum hydroxide, calcium silicate or polyamide powder may be used as a carrier ingredient. In particular, propellants such as chlorofluorocarbon, propane, butane or dimethyl ether may be further included.

When the formulation of the composition is solution or emulsion, solvents, solvating or emulsifying agents may be used as a carrier ingredient. For example, Water, ethanol, isopropanol, ethyl carbonate, ethyl acetate, benzyl alcohol, benzyl benzoate, propylene glycol, 1,3-butyl glycol oil, glycerol aliphatic esters, polyethylene glycol or fatty acid esters of sorbitan may be used.

When the formulation of the composition is suspension, liquid diluents such as water, ethanol, and propylene glycol, suspension such as ethoxylated isostearyl alcohols, polyoxyethylene sorbitol esters, and polyoxyethylene sorbitan esters, microcrystalline cellulose, aluminum metahydroxide, bentonite, agar or tragacanth may be used as a carrier ingredient The present invention will be further described with reference to the following examples, but it should be apparent that the present invention is not limited by the following examples.

Preparation Example 1: Preparation of Fermented Product Using *Lactobacillus* Strain A skim milk powder medium was inoculated with a *Lactobacillus plantarum* strain, and cultured at 37° C. for 3 days. After culture, centrifugation was performed to obtain a supernatant. The pH of the supernatant was adjusted to 6.5.

The supernatant was subjected to lyophilization to obtain a fermented product. The composition of skim milk powder medium is shown in Table 1 below.

TABLE 1

| Ingredient | Concentration (g/L) |
| --- | --- |
| Skim milk powder | 100 |
| Glucose | 20 |
| Yeast extract | 3 |
| Peptone | 3 |
| Distilled water | 1 |

Preparation Example 2: Preparation of Natural Extract (Hot Water Extraction)

Citrus (Citrus unshiu Marcov.) peel, Glycine max embryo, Nelumbo nucifera, mulberry root, and Ziziphus jujube Mill were each washed, dried at room temperature, and pulverized to obtain 100 g of a coarsely pulverized product for each component.

100 g of each of the pulverized products was immersed in purified water having a volume of 10 times the volume of the pulverized product, and reflux-extracted at 80° C. for 12 hours. The extract was filtered through a fine filter, and the remaining raw material was extracted three times in the same manner, and then cooled at room temperature. Each of the extracts was concentrated under reduced pressure at 30° C., and lyophilized to obtain a solid matter.

Preparation Example 3: Preparation of Natural Extract (Ethanol Extraction)

Each extract was obtained in the same manner as in Preparation Example 2, except that an ethanol aqueous solution (70% mass concentration) was used as an extraction solvent. Each extract was concentrated under reduced pressure and then lyophilized to obtain a solid matter.

Preparation Example 4: Preparation of Natural Extract (Alkaline Ionized Water Extraction)

Each extract was obtained in the same manner as in Preparation Example 2, except that alkaline ionized water was used as an extraction solvent. Each extract was concentrated under reduced pressure and then lyophilized to obtain a solid matter.

Example 1: Mixed Extract (Hot Water Extraction) Sample

The extracts of Preparation Examples 1 and 2 obtained by lyophilization were mixed in the same ratio. 10 g of the mixed extract was used as the sample of Example 1.

Example 2: Mixed Extract (Ethanol Extraction) Sample

The extracts of Preparation Examples 1 and 3 obtained by lyophilization were mixed in the same ratio. 10 g of the mixed extract was used as the sample of Example 2.

Example 3: Mixed Extract (Alkaline Ionized Water Extraction) Sample

The extracts of Preparation Examples 1 and 4 obtained by lyophilization were mixed in the same ratio. 10 g of the mixed extract was used as the sample of Example 3.

Comparative Example 1: *Lactobacillus*-Fermented Product Sample 10 g of the *Lactobacillus*-fermented product of Preparation Example 1 obtained by lyophilization was used as the sample of Comparative Example 1.

Comparative Example 2: Citrus (Citrus Unshiu Marcov.) Peel Extract (Hot Water Extraction) Sample 10 g of the citrus (Citrus unshiu Marcov.) peel extract of Preparation Example 1 obtained by lyophilization was used as the sample of Comparative Example 2.

Comparative Example 3: Glycine Max Embryo Extract (Hot Water Extraction) Sample 10 g of the Glycine max embryo extract of Preparation Example 2 obtained by lyophilization was used as the sample of Comparative Example 3.

Comparative Example 4: Nelumbo Nucifera Extract (Hot Water Extraction) Sample 10 g of the Nelumbo nucifera extract of Preparation Example 2 obtained by lyophilization was used as the sample of Comparative Example 4.

Comparative Example 5: Ziziphus Jujube Mill Extract (Hot Water Extraction) Sample 10 g of the Ziziphus jujube Mill extract of Preparation Example 2 obtained by lyophilization was used as the sample of Comparative Example 5.

Experimental Example 1: Evaluation of Effect of Promoting Papilla Cell Proliferation PVG rat vibrissa dermal papilla cells were transfected with a polyomavirus large T gene encoding a temperature-sensitive T antigen, and the effect of promoting papilla cell proliferation was evaluated using the papilla cells.

The papilla cells were inoculated into a 6 well plate at $1\times10^4$ cells/well and cultured. Each extract of the examples and the comparative examples was dissolved in dimethyl sulfoxide (DMSO) or ethanol, and the final concentration of the extract was adjusted to 10 ppm by serial dilution using DMEM medium containing 5% FBS.

200 μL of medium containing each of the extracts of the examples and the comparative examples was added to each well of the plate, and cultured at 37° C. for about 3 days in an incubator with 5% $CO_2$. After culture, 50 μL of MTT solution was added to each well, followed by incubation in the same incubator for 4 hours.

After the MTT reagent was absorbed into intracellular mitochondria, supernatants were removed, 150 μL of DMSO was added to each well, and cells were stained uniformly with a formazan dye by shaking for 10 minutes.

OD values at 515 nm were measured using an ELISA reader, and the number of cells was measured according to a standard curve prepared in advance. Based on the measured cell number, the effects (%) of the extracts of the examples and the comparative examples on papilla cell proliferation were evaluated. The results are shown in Table 2.

TABLE 2

| Classification | Effect of promoting cell proliferation (%) |
|---|---|
| Example 1 | 54.5 ± 1.1 |
| Example 2 | 61.6 ± 1.3 |
| Example 3 | 65.5 ± 1.2 |
| Comparative Example 1 | 23.1 ± 1.1 |
| Comparative Example 2 | 19.2 ± 1.2 |
| Comparative Example 3 | 16.6 ± 0.9 |
| Comparative Example 4 | 21.5 ± 1.3 |
| Comparative Example 5 | 18.5 ± 1.0 |

Referring to Table 2, compared to the single extracts of Comparative Examples 1 to 6, the extracts of Examples 1 to 3 exhibited much better effects on promoting papilla cell proliferation. In particular, compared to the extract of Example 2, the extract of Example 1, which was extracted using ethanol and alkaline ionized water as a solvent, exhibited a better effect on promoting cell proliferation. Thus, the extract prepared by ethanol and alkaline ionized water extraction is evaluated as excellent in preventing hair loss and promoting hair growth.

Experimental Example 2: Evaluation of Capillary Vasodilation Effect

To evaluate the capillary vasodilation effects of the extracts of the examples and the comparative examples, the effects of the extracts on proliferation of fibroblasts were measured. When potassium channels are activated, mitogenesis is promoted, and vascular smooth muscles relax and vasodilation is induced. On the other hand, when potassium channels are blocked, proliferation of NIH3T3 fibroblasts is promoted. Therefore, it is possible to confirm whether the potassium channel is opened by evaluating the degree of proliferation of fibroblasts.

To evaluate the effect of the extract on capillary vasodilatation, a DMEM medium containing 10% fetal calf serum (FCS) and 2 mM L-glutamine, and excluding any antibiotic was added to each well of a 24 well culture plate, and NIH3T3 fibroblasts were inoculated into the 24 well culture plate at $1\times10^4$ cells/well, followed by culture for 24 hours.

The cultured medium was replaced with a medium containing each extract of the examples and the comparative examples prepared in the same manner as in Experimental Example 1, and further cultured for 72 hours. After culture, the medium was removed, cells were washed with PBS ($Ca^{2+}/Mg^{2+}$ free) and treated with 0.5 ml of trypsin-ethylenediamine tetraacetic acid (TE), followed by incubation. Subsequently, DMEM containing 10% FCS was added to inactivate trypsin. Then, cells were detached from each well of the plate, placed in an EP tube, and centrifuged at 5,500 rpm. After centrifugation, the supernatant was removed, and remaining cells were suspended in 100 μL of PBS, and then the number of cells was counted using a hemocytometer. Based on the obtained results, the effects of the extracts of the examples and the comparative examples on capillary vasodilation were evaluated. The results are shown in Table 3 below.

TABLE 3

| Classification | Capillary vasodilation effect (%) |
|---|---|
| Example 1 | 43.5 ± 2.1 |
| Example 2 | 51.7 ± 1.3 |

TABLE 3-continued

| Classification | Capillary vasodilation effect (%) |
|---|---|
| Example 3 | 59.2 ± 1.6 |
| Comparative Example 1 | 17.1 ± 1.2 |
| Comparative Example 2 | 12.7 ± 1.1 |
| Comparative Example 3 | 11.4 ± 0.9 |
| Comparative Example 4 | 14.5 ± 1.4 |
| Comparative Example 5 | 16.3 ± 1.0 |

Referring to Table 3, compared to the single extracts of Comparative Examples 1 to 5, the mixed extracts of Examples 1 to 3 exhibited much better effects on capillary vasodilation.

In particular, compared to the extract of Example 1, the extracts of Examples 2 and 3, which were extracted using ethanol and alkaline ionized water, exhibited much better effects on capillary vasodilation. Thus, the extract prepared by ethanol and alkaline ionized water extraction is evaluated to improve blood circulation of the capillary blood vessels in the scalp, thereby improving hair health and inhibiting hair loss.

Experimental Example 3: Evaluation of Hair Growth Promoting Effect

Hair was removed from approximately 50-day-old mice (C57BL/6) of which hair was at telogen, and the effects of the extracts of the examples and the comparative examples on promoting hair growth were evaluated.

In this experiment, mice with similar characteristics such as body weight and size were divided into 9 groups of 10 mice and individually raised. The growth of hair was measured in the mice.

Mice were fed cereal feed containing 1.0% by weight of each extract of the examples and the comparative examples, and bred for 30 days. Then, hair grown in an epilated region was separated and weighed. Mice fed cereal feed containing no extract were used as a control group to more clearly evaluate the effect of the extract on hair growth. The results are shown in Table 4.

TABLE 4

| Classification | Hair Weight (mg) |
|---|---|
| Example 1 | 236.1 ± 11.8 |
| Example 2 | 245.5 ± 12.3 |
| Example 3 | 259.2 ± 12.3 |
| Comparative Example 1 | 112.9 ± 8.1 |
| Comparative Example 2 | 89.6 ± 9.3 |
| Comparative Example 3 | 85.2 ± 7.6 |
| Comparative Example 4 | 95.3 ± 9.6 |
| Comparative Example 5 | 92.6 ± 8.4 |
| Control group | 53.7 ± 6.5 |

Referring to Table 4, compared to the single extracts of Comparative Examples 1 to 5, the mixed extracts of Examples 1 to 3 exhibited much better effects on promoting hair growth. In particular, compared to the extract of Examples 1, the extracts of Examples 2 and 3, which were extracted using ethanol and alkaline ionized water, exhibited much better effects on promoting hair growth. Thus, the extract prepared by ethanol and alkaline ionized water extraction is evaluated to improve hair health and inhibit hair loss.

Experimental Example 4: Evaluation of Free Radical Scavenging Activity

The extracts of the examples and the comparative examples were suspended in purified water (at a concentration of 10%), and the free radical scavenging activities thereof were evaluated.

DPPH assay is a method in which an inhibitor eliminates a stable radical, 2,2-diphenyl-1-picrylhydrazyl (DPPH), and the degree of discoloration is analyzed by measuring the absorbance at 540 nm.

Dibutyl hydroxy toluene (BHT) was used as a control for measurement of free radical scavenging activity. BHT is a colorless crystal or white crystalline powder, and has an excellent antioxidant effect and thus is widely used as an antioxidant for edible oil and fats, and foods containing oil or fats.

The experiment was repeated three times for accuracy, and the results are shown in Table 5 below.

TABLE 5

| Classification | DPPH radical scavenging activity (%) |
|---|---|
| Example 1 | 135.1 |
| Example 2 | 146.7 |
| Example 3 | 151.9 |
| Comparative Example 1 | 112.2 |
| Comparative Example 2 | 109.3 |
| Comparative Example 3 | 105.5 |
| Comparative Example 4 | 94.7 |
| Comparative Example 5 | 93.8 |
| Control group | 157.5 |

Referring to Table 5, in the case of Examples 1 to 3, the concentration of the extract and the free radical scavenging activity thereof were proportional, and the free radical scavenging activity was significantly superior to that of Comparative Examples 1 to 5.

High free radical scavenging activity may indicate that the antioxidant effect is excellent. In particular, the extracts of Examples 2 and 3, which were prepared using ethanol and alkaline ionized water extraction, showed an excellent antioxidant effect as compared to that of Example 1.

Experimental Example 5: Evaluation of Anti-Inflammatory Activity

The inhibitory activity of EAME on NO production was examined in RAW 264.7 cells, a murine macrophage cell line, stimulated with lipopolysaccharide (LPS), and the anti-inflammatory activities of the extracts of the examples and the comparative examples were evaluated.

Raw 264.7 cells were obtained from the Korean Cell Line Bank. Raw 264.7 cells were cultured in a DMEM medium containing 100 units/mL penicillin-streptomycin and 10% fetal bovine serum (FBS) in a $CO_2$ incubator set to 37° C. with 5% $CO_2$, and subcultured every 2 to 3 days.

Raw 264.7 cells (at a cell density of $3 \times 10^5$ cells/mL) were pre-cultured for 18 hours, treated with the extract samples (at a concentration of 10%) of the examples and the comparative examples and LPS (1 μg/mL) at the same time, and further cultured for 24 hours. After culture, to determine the amount of produced NO, the amount of $NO_2^-$ present in the cell culture medium was measured using a Griess reagent. A negative control group was not treated with LPS, and a positive control group was treated only with LPS.

100 μL of the cell culture supernatant and 100 μL of a Griess reagent (1% (w/v) sulfanilamide and 0.1% (w/v) naphtylehtylenediamine in 2.5% (v/v) phosphoric acid) were mixed and reacted at room temperature for 10 minutes under dark conditions. After reaction, absorbance was measured at 540 nm using a ELISA reader. A standard concentration curve was obtained using serial dilution of sodium nitrite ($NaNO_2$) (10-100 μM). The results are shown in Table 6 below.

TABLE 6

| Classification | Amount of NO production (μM) |
|---|---|
| Example 1 | 14.35 |
| Example 2 | 12.75 |
| Example 3 | 11.42 |
| Comparative Example 1 | 23.34 |
| Comparative Example 2 | 25.78 |
| Comparative Example 3 | 23.28 |
| Comparative Example 4 | 28.34 |
| Comparative Example 5 | 26.61 |
| LPS (−) | 6.98 |
| LPS (+) | 36.64 |

Referring to Table 6, compared to the single extracts of Comparative Examples 1 to 5, the mixed extracts of Examples 1 to 3 exhibited a higher inhibitory activity against nitric oxide (NO) production and had excellent antioxidant and anti-inflammatory activities.

Experimental Example 6: Evaluation of Antimicrobial Activity

The antimicrobial activities of the samples obtained according to the examples and the comparative examples were evaluated. *Pityrosporum ovale* ATCC 12087 was used as a published strain, and triclosan, a chemical synthetic antimicrobial agent, was used as a positive control.

*Propionibacterium acnes* KCTC 3314 was streaked onto a tryptic soy agar medium containing 5% sheep blood and incubated for about 2 to 3 days. Bacterial concentration was $1 \times 10^8$ cells/mL when the turbidity of the bacteria was equal to the turbidity of 0.5 McFarland Nephelometer Standard (1% barium chloride (0.05 ml)+1% sulfuric acid (9.95 ml)).

Each sample was diluted to 2 ml of BHI broth at a concentration of 0 to 2,000 ppm using a 100-ppm dilution interval. Then, the diluted sample was inoculated with 20 μL of the bacteria-containing solution at a cell density of $1 \times 10^8$ cells/mL and cultured for 48 hours. The minimum concentration that inhibits bacterial growth based on turbidity was defined as the minimum inhibitory concentration (MIC), and the results are shown in Table 7 below.

TABLE 7

| Classification | Minimum inhibitory concentration (MIC) (ppm) |
|---|---|
| Example 1 | 650 |
| Example 2 | 550 |
| Example 3 | 520 |
| Comparative Example 1 | 1,100 |
| Comparative Example 2 | 1,300 |
| Comparative Example 3 | 1,500 |
| Comparative Example 4 | 1,700 |
| Comparative Example 5 | 1,400 |
| Triclosan | 400 |

Referring to Table 7, compared to triclosan, a positive control, the mixed extracts of Examples 1 to 3 exhibited a slightly weaker antimicrobial effect, but exhibited a remarkably superior antimicrobial effect as compared to the extracts of Comparative Examples 1 to 5.

In particular, the extracts of Examples 2 and 3, which were obtained by using ethanol and alkaline ionized water extraction, had better antimicrobial effects against dandruff-inducing microorganism, compared to the extract of Example 1.

The aforementioned description of the present invention is provided by way of example and those skilled in the art will understand that the present invention can be easily changed or modified into other specified forms without change or modification of the technical spirit or essential characteristics of the present invention. Therefore, it should be understood that the aforementioned examples are only provided by way of example and not provided to limit the present invention. For example, each of constituents described as a single form may be separately implemented and, similarly, constituents described as being separated may be implemented in a combined form.

It should be understood that the scope of the present invention is defined by the following claims and the invention is to cover all modifications, equivalents, and alternatives falling within the spirit and scope of the invention as defined by the claims.

It should be understood that the effects of the present invention are not limited to the effects described above, and include all effects that can be deduced from the description of the invention or the composition of the invention described in the claims.

When the composition for preventing hair loss and promoting hair growth according to one aspect of the invention is used, through interaction of the active ingredients contained in the mixed extract, the skin health of the user can be improved, and the effect of inhibiting hair loss and promoting hair growth can be maximized.

What is claimed is:

1. A composition for reducing hair loss and promoting hair growth, comprising a mixed extract consisting of a *Lactobacillus*-fermented product, a citrus (Citrus unshiu Marcov.) peel extract, a Glycine max embryo extract, a Nelumbo nucifera extract, and a Ziziphus jujube Mill extract as an active ingredient, wherein the *Lactobacillus*-fermented product, the citrus (Citrus unshiu Marcov.) peel extract, the Glycine max embryo extract, the Nelumbo nucifera extract, and the Ziziphus jujube Mill extract are contained at a weight ratio of 1:1:1:1:1.

2. The composition according to claim 1, wherein the mixed extract is contained in the composition in an amount of 0.5 to 10.0% by weight.

3. The composition according to claim 1, wherein the mixed extract is extracted using 60 to 90% (v/v) ethanol.

4. The composition according to claim 1, wherein the composition has anti-inflammatory and antimicrobial activities and an ability to promote cell proliferation.

5. The composition according to claim 1, wherein the composition is formulated into one or more products selected from the group consisting of hair toner, hair lotion, hair cream, hairspray, hair mousse, hair gel, hair soap, hair shampoo, hair conditioner, hair pack, and hair treatment.

6. The composition according to claim 5, wherein the composition is formulated into a product which is a liquid hair shampoo.

7. The composition according to claim 2, wherein the composition has anti-inflammatory and antimicrobial activities and an ability to promote cell proliferation.

8. The composition according to claim 3, wherein the composition has anti-inflammatory and antimicrobial activities and an ability to promote cell proliferation.

9. The composition according to claim 2, wherein the composition is formulated into one or more products selected from the group consisting of hair toner, hair lotion, hair cream, hairspray, hair mousse, hair gel, hair soap, hair shampoo, hair conditioner, hair pack, and hair treatment.

10. The composition according to claim 3, wherein the composition is formulated into one or more products selected from the group consisting of hair toner, hair lotion, hair cream, hairspray, hair mousse, hair gel, hair soap, hair shampoo, hair conditioner, hair pack, and hair treatment.

* * * * *